US012740939B2

(12) United States Patent
Betser et al.

(10) Patent No.: US 12,740,939 B2
(45) Date of Patent: Sep. 22, 2026

(54) ELASTOMERIC MATRICES BASED ON PLASTICIZED PVOH COMPOSITIONS AND USES THEREOF

(71) Applicant: aVISI Ltd., Tel-Aviv (IL)

(72) Inventors: Nir Betser, Tel-Aviv (IL); Itai Adin, Beer-Sheva (IL); Keren Hadar, Holon (IL)

(73) Assignee: aVISI Ltd., Tel-Aviv (IL)

( * ) Notice: Subject to any disclaimer, the term of this patent is extended or adjusted under 35 U.S.C. 154(b) by 319 days.

(21) Appl. No.: 18/702,821

(22) PCT Filed: Oct. 27, 2022

(86) PCT No.: PCT/IL2022/051138

§ 371 (c)(1),
(2) Date: Apr. 19, 2024

(87) PCT Pub. No.: WO2023/073707

PCT Pub. Date: May 4, 2023

(65) Prior Publication Data

US 2024/0415763 A1 Dec. 19, 2024

Related U.S. Application Data

(60) Provisional application No. 63/272,241, filed on Oct. 27, 2021.

(30) Foreign Application Priority Data

Oct. 27, 2021 (IL) ......................................... 287646

(51) Int. Cl.

| | |
|---|---|
| ***A61K 9/00*** | (2006.01) |
| ***A61K 47/32*** | (2006.01) |
| ***C08K 5/053*** | (2006.01) |
| ***C08L 29/04*** | (2006.01) |
| ***C08L 71/02*** | (2006.01) |

(52) U.S. Cl.

CPC ............ *A61K 9/0051* (2013.01); *A61K 47/32* (2013.01); *C08K 5/053* (2013.01); *C08L 29/04* (2013.01); *C08L 71/02* (2013.01); *C08L 2205/06* (2013.01)

(58) Field of Classification Search

None

See application file for complete search history.

(56) References Cited

U.S. PATENT DOCUMENTS

| | | | |
|---|---|---|---|
| 3,416,530 A | 12/1968 | Ness | |
| 3,828,777 A | 8/1974 | Ness | |
| 3,868,445 A | 2/1975 | Ryde et al. | |
| 4,014,335 A | 3/1977 | Arnold | |
| 4,119,604 A | 10/1978 | Wysong | |
| 4,409,205 A * | 10/1983 | Shively | A61K 31/77 514/23 |
| 4,540,408 A | 9/1985 | Lloyd | |
| 4,663,358 A | 5/1987 | Hyon et al. | |
| 4,874,562 A | 10/1989 | Hyon et al. | |
| 4,966,924 A | 10/1990 | Hyon et al. | |
| 5,773,021 A | 6/1998 | Gurtler et al. | |
| 6,217,896 B1 | 4/2001 | Benjamin | |
| 8,679,078 B2 | 3/2014 | Leahy et al. | |
| 9,724,230 B2 | 8/2017 | Badawi | |
| 10,010,502 B2 | 7/2018 | Leahy et al. | |
| 10,513,588 B2 * | 12/2019 | Friedrich | C11D 17/044 |
| 2005/0010010 A1 | 1/2005 | Kitamura et al. | |
| 2005/0049323 A1 | 3/2005 | Gvozdic | |
| 2005/0095296 A1 * | 5/2005 | Lowman | G10K 11/02 600/437 |
| 2010/0234784 A1 | 9/2010 | Hartwell | |
| 2019/0338089 A1 | 11/2019 | Childers et al. | |
| 2022/0168142 A1 | 6/2022 | Saim et al. | |

FOREIGN PATENT DOCUMENTS

| | | |
|---|---|---|
| CN | 103006620 A * | 4/2013 |
| CN | 104356569 | 2/2015 |
| CN | 105524384 | 4/2016 |
| CN | 112143148 | 12/2020 |
| EP | 1189595 | 5/2003 |
| KR | 10-2022-0110912 | 8/2022 |
| WO | WO 2006/037157 | 4/2006 |
| WO | WO 2008/014573 | 2/2008 |
| WO | WO 2022/016268 | 1/2022 |
| WO | WO 2023/073707 | 5/2023 |
| WO | WO 2024/224394 | 10/2024 |

OTHER PUBLICATIONS

International Search Report and the Written Opinion Dated Jul. 25, 2024 From the International Searching Authority Re. Application No. PCT/IL2024/050391 (30 Pages).

Mali et al. "Polyvinyl Alcohol Films With Different Degrees of Hydrolysis and Polymerization", Semina Ciencias Exatas e Tecnologicas, 40(2): 169-178, XP093180190, Dec. 18, 2019.

Maria et al. "The Effect of the Degree of Hydrolysis of the PVA and the Plasticizer Concentration on the Color, Opacity, and Thermal and Mechanical Properties of Films Based on PVA and Gelatin Blends", Journal of Food Engineering, 87(2): 191-199, XP022496969, Jul. 2008.

Communication Pursuant to Article 94(3) EPC Dated Aug. 11, 2025 From the European Patent Office Re. Application No. 24204484.0. (4 Pages).

(Continued)

*Primary Examiner* — Robert A Wax

*Assistant Examiner* — William Craigo

(57) ABSTRACT

Provided herein is an elastomeric matrix which includes poly(vinyl alcohol) (PVOH), at least two plasticizers none of which is water, and water. The combined mass ratio of plasticizers to PVOH is at least 2:1; and the combined mass content of PVOH and plasticizers is at least 70% by weight of the total weight of the matrix excluding water.

20 Claims, No Drawings

(56) References Cited

OTHER PUBLICATIONS

Mirzaeei et al. "Design and Evaluation of Soluble Ocular Insert for Controlled Release of Chloramphenicol", Journal of Reports in Pharmaceutical Sciences, 6(2): 123-133, Published Online Jul. 3, 2017.
Özdemir et al. "Preparation and Characterization Studies of Dorzolamide-Loaded Ophthalmic Implants for Treating Glaucoma", Turkish Journal of Pharmaceutical Sciences, 20(3): 149-156, Jul. 7, 2023.
Communication Pursuant to Article 94(3) EPC Dated Nov. 6, 2023 From the European Patent Office Re. Application No. 22814192.5 (3 Pages).
International Preliminary Report on Patentability Dated May 10, 2024 From the International Bureau of WIPO Re. Application No. PCT/IL2022/051138 (7 Pages).
International Search Report and the Written Opinion Dated Jul. 4, 2024 From the International Searching Authority Re. Application No. PCT/II.2024/050392. (11 Pages).
International Search Report and the Written Opinion Dated Jan. 31, 2023 From the International Searching Authority Re. Application No. PCT/IL2022/051138 (10 Pages).
Office Action Dated Apr. 10, 2022 From the Israel Patent Office Re. Application No. 287646. (9 Pages).
Bajgrowicz et al. "Release of Ciprofloxacin and Moxifloxacin From Daily Disposable Contact Lenses From An In Vitro Eye Model", Investigative Ophthalmology & Visual Science, 56(4): 2234-2242, Apr. 1, 2015.
Buehler et al. "Nelfilcon A, A New Material for Contact Lenses", Chimia, 53(6): 269-274, Jun. 29, 1999.
Fong et al. "The Impact of Plasticizer and Degree of Hydrolysis on Free Volume of Poly(Vinyl Alcohol) Films", Polymers, 10(9) 1036: 1-15, Sep. 18, 2018.
Jang et al. "Plasticizer Effect on the Melting and Crystallization Behavior of Polyvinyl Alcohol", Polymer, 44(26): 8139-8146, Dec. 1, 2003.
Lim et al. "The Effect of Plasticizers on the Properties of Polyvinyl Alcohol Films", Drug Development and Industrial Pharmacy, 20(6):1007-1020, Jan. 1, 1994.
Mohsin et al. "Thermal and Mechanical Properties of Poly(Vinyl Alcohol) Plasticized With Glycerol", Journal of Applied Polymer Science, 122(5): 3102-3109, Published Online Jul. 7, 2011.
Otsuka et al. "A Simple Method to Obtain A Swollen PVA Gel Crosslinked by Hydrogen Bonds", Journal of Applied Polymer Science, 114(1): 10-16, Published Online May 27, 2009.
Pan et al. "Study on Mechanical and Optical Properties of Poly(Vinyl Alcohol) Hydrogel Used as Soft Contact Lens", Materials Technology: Advanced Performance Materials, 31 (5): 266-273, Published Online Feb. 2, 2016.
Riedo et al. "Poly(Vinylalcohol)-Borate Hydrogels With Iimproved Features for the Cleaning of Cultural Heritage Surfaces", Heritage Science, 3(1): 23-1-23-11, Dec. 2015.
Rivera-Hernandez et al. "Polyvinyl Alcohol Based-Drug Delivery Systems for Cancer Treatment", International Journal of Pharmaceutics, 600: 120478-1-120478-11, Available Online Mar. 12, 2021.
Shi et al. "Facile Preparation of Hydrogen-Bonded Supramolecular Polyvinyl Alcohol-Glycerol Gels With Excellent Thermoplasticity and Mechanical Properties", Polymer, 111: 168-176, Feb. 24, 2017.
Wu et al. "Influence of Polyol Plasticizers on the Properties of Polyvinyl Alcohol Films Fabricated by Melt Processing", Journal of Polymers and the Environment, 20(1): 63-69, Published Online Sep. 22, 2011.
Zhang et al. "The Instructive Role of Mechanical Properties of Polyvinyl Alcohol Film in the Process of YS7. Tape Calendering", Ceramics International, 46(10/Pt.B): 17010-17017, Jul. 2020.
Supplementary European Search Report and the European Search Opinion Dated Feb. 4, 2026 From the European Patent Office Re. Application No. 25216421.5. (9 Pages).

* cited by examiner

ELASTOMERIC MATRICES BASED ON PLASTICIZED PVOH COMPOSITIONS AND USES THEREOF

RELATED APPLICATIONS

This application is a National Phase of PCT Patent Application No. PCT/IL2022/051138 having International filing date of Oct. 27, 2022, which claims the benefit of priority of Israeli Patent Application No. 287646 and under 35 USC § 119(e) of U.S. Provisional Patent Application No. 63/272,241, both filed on Oct. 27, 2021.

The contents of the above applications are all incorporated herein by reference as if fully set forth herein in their entirety.

FIELD AND BACKGROUND OF THE INVENTION

The present invention, in some embodiments thereof, relates to material science, and more particularly, but not exclusively, to a polyvinyl alcohol (PVOH) based elastomeric matrix and uses thereof.

Polyvinyl alcohol (PVOH) is water-soluble synthetic polymer represented by the formula $(C_2H_4O)n$. It is prepared by hydrolysis of polyvinyl acetates, which replaces the acetate groups with hydroxyl groups. PVOH has numerous applications, including biomedical and pharmaceutical applications such as artificial heart linings, artificial cartilages, catheters, skin and pancreas membranes. PVOH may be chemically or physically (i.e., not by covalent bonds) crosslinked.

During physical crosslinking, hydroxyl groups interact to form intra- and intermolecular hydrogen bonds resulting in formation of crystallites. Physical crosslinking is typically carried out by freeze-thaw with or without addition of solvents, resulting in the well-known cryogels. Alternatively, solutions of polyvinyl alcohol can be dried (Otsuka, E., & Suzuki, A., *Journal of Applied Polymer Science,* 2009, 114(1), 10-16, doi:10.1002/app.30546]. Various plasticizers can be added to improve flexibility, and the amount added is commonly less than 30%, often less than 10% [Mohsin, M., et al., *Journal of Applied Polymer Science,* 2011, 122(5), 3102-3109. doi:10.1002/app.34229; Lim, L. Y. et al., *Drug Development and Industrial Pharmacy,* 1994, 20(6), 1007-1020. doi:10.3109/03639049409038347; and Wu, W. et al., *Journal of Polymers and the Environment,* 2011, 20(1), 63-69. doi:10.1007/s10924-011-0364-7].

Zhang, B. et al., [*Ceramics International,* 2020, doi: 10.1016/j.ceramint.2020.03.286] teach about the instructive role of mechanical properties of polyvinyl alcohol film in the process of YSZ tape calendaring.

U.S. Pat. No. 4,874,562 discloses a method of molding a polyvinyl alcohol contact lens.

U.S. Pat. No. 4,663,358 discloses a porous and transparent hydrated gel that is prepared from a poly(vinyl alcohol) solution in a mixed solvent consisting of water and a water-miscible organic solvent. Upon cooling the poly(vinyl alcohol) solution below room temperature, a gel is formed as a consequence of crystallization of poly(vinyl alcohol) molecules. Exchange of the organic solvent included in the gel with water produces a hydrated gel of poly(vinyl alcohol) which has a high tensile strength, a high water content, and a high light transmittance.

U.S. Pat. No. 10,513,588 discloses water-soluble polyvinyl alcohol film with plasticizer blend.

SUMMARY OF THE INVENTION

The present disclosure provides an elastomeric matrix formed from polyvinyl alcohol and plasticizers. The herein-disclosed elastomeric matrix is soft and elastic in its dry form. The matrix may be stored for long periods under dry conditions without losing its softness and plasticity, and thus may enjoy particularly long shelf life. The matrix substantially does not change properties, such as shape, volume, and elasticity, after being immersed or exposed to liquid, and thus may be suitable for applications that require such stability. The elastomeric matrix can be loaded with additional compounds, such as pharmaceutically active agents, and can be used as or in an ophthalmic device. Some embodiments of the matrix disclosed herein may be used as implants, for topical application, or for insertion into body cavities. Some embodiments may be self-applied or applied by a physician, for example, during chirurgical procedure.

Thus, according to an aspect of some embodiments of the present invention, there is provided an elastomeric matrix that includes:

poly(vinyl alcohol) (PVOH), at least two plasticizers none of which is water, and water, wherein:

a combined mass ratio of the plasticizers to the PVOH is at least 2:1; and a combined mass content of the PVOH and the plasticizers is at least 70% wt of the total weight of the matrix excluding the water.

According to another aspect of some embodiments of the present invention, there is provided an elastomeric matrix for use as an ophthalmic device, which includes:

poly(vinyl alcohol) (PVOH), at least one plasticizer which is not water, and water, wherein:

a mass ratio of the plasticizer to the PVOH is at least 2:1; and a combined mass content of the PVOH and the plasticizer is at least 70% wt of the total weight of the matrix excluding the water.

In some embodiments, the elastomeric matrix provided herein includes at least two plasticizers, none of which is water.

In some embodiments, the mass ratio of the plasticizer to the PVOH is less than 20:1.

In some embodiments, the elastomeric matrix provided herein is characterized by substantially isotropic swelling and shrinking.

In some embodiments, the elastomeric matrix provided herein is characterized by having substantially the same shape under wet or dry conditions (shape stability; shape invariability; shape retention).

In some embodiments, the elastomeric matrix provided herein is characterized by swelling by less than 50% by volume under wet conditions.

In some embodiments, the elastomeric matrix provided herein is characterized by a degree of crystallinity lower than 50%.

In some embodiments, the elastomeric matrix provided herein is characterized by total light transmittance of less than 80%.

In some embodiments, the PVOH is characterized by a degree of hydrolysis of more than 90%.

In some embodiments, the PVOH is characterized by a degree of polymerization between 500 and 5000.

In some embodiments, the plasticizer or plasticizers include at least two hydrogen bond forming functional groups.

In some embodiments, the plasticizer or plasticizers is characterized by a molar mass of less than 1,000 g/mol.

In some embodiments in which the matrix includes more than one plasticizers, at least one of the plasticizers is an oligomer characterized by a molar mass of more than 1,000 g/mol.

In some embodiments in which the matrix includes more than one plasticizers, at least one of the plasticizers is characterized by a viscosity of at least 1000 cp, and at least one other of the plasticizers is characterized by a viscosity of less than 200 cp.

In some embodiments, the plasticizer is independently selected from the group consisting of a polyol, a polyprotic organic acid, a polyamine, an alkyl gluceth, an aliphatic polyalkylene glycol, an ethanolamine, a saccharide, an oligosaccharide, an amino acid, a polyphenol, tromethamine, urea, tannic acid, and any salt thereof and/or combinations thereof.

In some embodiments, the polyol is selected from the group consisting of ethylene glycol, diethylene glycol, triethylene glycol, tetraethylene glycol, propylene glycol, triacetin erythritol, a poly-glycol, a poloxamer, and a copolymer thereof, and glycerol and esters thereof.

In some embodiments, the polyprotic organic acid is selected from the group consisting of oxalic acid, maleic acid, citric acid, and any salt thereof.

In some embodiments, the polyamine is selected from the group consisting of spermine, spermidine, diethylenetriamine, triethylenetetramine, tris(2-aminoethyl)amine, a polyethylenimine, and any salt thereof.

In some embodiments, the aliphatic polyalkylene glycol is selected from the group consisting of a polyethylene glycol, a polypropylene glycol, a poly-glycol, a poloxamer, and a polysorbate.

In some embodiments, the aliphatic polyalkylene glycol is polyethylene glycol.

In some embodiments, the mass content of the PVOH is substantially equal to a mass content of the aliphatic polyalkylene glycol.

In some embodiments, the aliphatic polyalkylene glycol is selected from the group consisting of polyethylene glycol, polypropylene glycol, and any mixture thereof.

In some embodiments, the plasticizer is biocompatible.

In some embodiments, the plasticizer is ophthalmically acceptable.

According to some embodiments, the plasticizer in the elastomeric matric provided herein are any one of glycerol, propylene glycol, sugar alcohols such as mannitol and sorbitol, citrate salt, and EDTA salt. In some embodiments, PEG and polypropylene glycol represent preferred second plasticizers. Other preferred plasticizers include di-carboxylic acids, such as maleic acid, fumaric acid, tannic acid, etc., sugars, such as fructose, maltose, etc., DMSO, amino acids, tri-ethyl citrate, and di-propylene glycol.

According to some embodiments, the mechanical properties of the elastomeric matric provided herein include Young modulus of 0.05-2 MPa, tensile strength of 0.05-2 MPa, and elongation at break of 100-900%.

In some embodiments, the mass content of water constitutes less than 50% wt of the total mass content of the elastomeric matrix of provided herein.

In some embodiments, the mass content of PVOH constitutes less than 5% wt of the total mass content of non-water ingredients of the elastomeric matrix of provided herein.

In some embodiments, the elastomeric matrix of provided herein is essentially devoid of covalent crosslinking.

In some embodiments, the elastomeric matrix of provided herein includes a non-PVOH polymer that is characterized by a plurality of hydrogen bond forming residues.

In some embodiments, the mass ratio of the PVOH to the non-PVOH polymer is at least 2:1.

In some embodiments, the non-PVOH polymer is selected from the group consisting of a polyacrylic acid, a polyvinyl pyrrolidone, a cellulose, a chitin, a glycogen, a starch, a gellan, a dextran, an inulin, a pectin, an arabinoxylan, and any mixture thereof.

In some embodiments, the matrix of provided herein further includes a pharmaceutically active agent.

According to another aspect of some embodiments of the present invention, there is provided an ophthalmic device that includes the elastomeric matrix of provided herein.

In some embodiments, the elastomeric matrix consists of ophthalmically acceptable ingredients.

In some embodiments, the elastomeric matrix includes a pharmaceutically active agent.

In some embodiments, the device is configured to be positioned on a surface of an eye.

In some embodiments, the surface is at least partially underneath at least one of the upper and lower eyelids and outside a cornea of the eye.

In some embodiments, the device is configured for delivering at least one pharmaceutically active agent to an eye for an extended period of time.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the phrases "substantially devoid of" and/or "essentially devoid of" in the context of a certain substance, refer to a composition that is totally devoid of this substance or includes less than about 5, 1, 0.5 or 0.1 percent of the substance by total weight or volume of the composition. Alternatively, the phrases "substantially devoid of" and/or "essentially devoid of" in the context of a process, a method, a property or a characteristic, refer to a process, a composition, a structure or an article that is totally devoid of a certain process/method step, or a certain property or a certain characteristic, or a process/method wherein the certain process/method step is effected at less than about 5, 1, 0.5 or 0.1 percent compared to a given standard process/method, or property or a characteristic characterized by less than about 5, 1, 0.5 or 0.1 percent of the property or characteristic, compared to a given standard.

When applied to an original property, or a desired property, or an afforded property of an object or a composition, the term "substantially maintaining", as used herein, means that the property has not change by more than 20%, 10% or more than 5% in the processed object or composition.

The term "exemplary" is used herein to mean "serving as an example, instance or illustration". Any embodiment described as "exemplary" is not necessarily to be construed as preferred or advantageous over other embodiments and/or to exclude the incorporation of features from other embodiments.

The words "optionally" or "alternatively" are used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the terms "process" and "method" refer to manners, means, techniques and procedures for accomplishing a given task including, but not limited to, those manners, means, techniques and procedures either known to, or readily developed from known manners, means, techniques and procedures by practitioners of the chemical, material, mechanical, computational and digital arts.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DESCRIPTION OF EMBODIMENTS OF THE INVENTION

The present invention, in some embodiments thereof, relates to material science, and more particularly, but not exclusively, to a polyvinyl alcohol (PVOH) based elastomeric matrix and uses thereof.

Before explaining at least one embodiment of the invention in detail, it is to be understood that the invention is not necessarily limited in its application to the details set forth in the following description or exemplified by the Examples. The disclosure is meant to encompass other embodiments or of being practiced or carried out in various ways.

While conceiving the present invention, the present inventors envisioned a PVOH-based elastomeric matrix that is free of chemical crosslinker residues and stable during soaking in aqueous medium in terms of shape and consistency. The envisioned elastomeric matrix was both soft and elastic under dry and wet conditions, and substantially did not change shape, after being immersed in or exposed to liquid. While reducing the present invention to practice, the present inventors have surprisingly found that such a matrix can be formed by adding to polyvinyl alcohol a large amount of plasticizers. Particularly, the amount of plasticizer (or plasticizers) should be at least twice that of the polyvinyl alcohol.

A PVOH-Based Elastomeric Matrix:

While optimizing the finding discussed hereinabove, it was surprisingly found by the present inventors that an elastomeric matrix comprising less than 35% by weight (% wt) of polyvinyl alcohol in the composition, maintains its elastomeric matrix form under dry conditions; swells by less than 50% by volume (or less than 15% along each of its three dimensions) under wet conditions and substantially maintains its size, shape and form when moving from dry to wet conditions and back. Manipulating these properties (e.g., decreasing the tendency to swell without compromising pliability), were found to require the use of at least two plasticizers.

Thus, according to an aspect of some embodiments of the present invention, there is provided an elastomeric matrix, which includes poly(vinyl alcohol) (PVOH), at least two plasticizers none of which is water, and water. The matrix exhibits particular desired properties when the combined mass ratio of the plasticizers with respect to PVOH is at least 2:1, and the combined mass content of PVOH and the plasticizers is at least 70% wt of the total weight of the matrix, excluding the mass of water, namely the total mass of the PVOH and the plasticizer(s) is at least 70% wt, at least 60% wt or at least 50% wt of the mass of all non-water ingredients of the matrix.

The term "combined mass ratio", as used herein, refers to the combined amount of a plurality ingredients (e.g., the plasticizers) relative to the amount of another ingredient of the matrix (e.g., the PVOH), wherein all the amounts are provided in terms of mass (e.g., gram). The combined mass ratio is calculated by summing the mass of the plurality of ingredients to obtain a combined mass; and dividing the combined mass by the mass of the other ingredient.

The term "combined mass", as used herein, refers to the combined amount of a plurality ingredients, provided in terms of mass. The combined mass is calculated by summing the masses of the ingredients making up the plurality.

According to another aspect of some embodiments of the present invention, there is provided an elastomeric matrix for use as an ophthalmic device, which includes poly(vinyl alcohol) (PVOH), a plasticizer which is not water, and water, wherein the mass ratio of the plasticizer to PVOH is at least 2:1, and the mass content of all non-water ingredients of the matrix is at least 70% wt of the total weight of the matrix excluding the mass of water. In some embodiments, the elastomeric matrix for use as an ophthalmic device includes at least two plasticizers, none of which is water, and the combined mass ratio of the plasticizers with respect to PVOH is at least 2:1, and the combined mass content of PVOH and the plasticizers is at least 70% wt of the total weight of the matrix, excluding the mass of water, namely the total mass of the PVOH and the plasticizer(s) is at least 70% wt, at least 60% wt or at least 50% wt of the mass of all non-water ingredients of the elastomeric matrix for use as an ophthalmic device.

In some embodiments, the mass ratio of the plasticizer(s) to PVOH is less than 5:1, less than 10:1, less than 15:1, less than 20:1, or less than 30:1. In some embodiments the mass ratio of the plasticizer(s) to PVOH ranges from 5-2:1 (from 5:1 to 2:1), or 30:1 to 5:1.

According to some embodiments of the present invention, the mass content of PVOH constitutes less than 5% wt of the total weight of non-water ingredients of the matrix. Alternatively, the mass content of PVOH constitutes less than 10% wt, less than 15% wt, less than 20% wt, less than 25% wt, or less than 30% wt of the total weight of non-water ingredients of the matrix.

The term "elastomeric matrix", as used herein, refers to a crosslinked polymeric structure form that displays rubber-like elasticity and can undergo deformation under the influence of a force and regain its original shape once the force has been removed. In the context of some embodiments of the present invention, the elastomeric matrix is a form of physically crosslinked polymeric structure having an open-cell porous microstructure that can incorporate sequestered and releasable substances within its interconnected voids. According to some embodiments of the present invention, the elastomeric matrix is a network of hydrogen-bonded polymers and plasticizers. According to some embodiments of the present invention, the elastomeric matrix is a network of hydrogen-bonded polymers, plasticizers and water. In some embodiments, the elastomeric matrix provided herein is essentially devoid of covalent crosslinking.

In some embodiments, the elastomeric matrix provided herein has a porosity of about 50-90%. In some embodiments, the matrix is characterized by a porosity of at least about 50%, 60%, 70%, 80% or at least about 90%.

The consistency of the elastomeric matrix provided herein may resemble that of a hydrogel, however, in distinction from hydrogels, the elastomeric matrix provided herein is stable under dry conditions, and does not have to be immersed in water in order to retain its pliability. The mechanical properties of the elastomeric matrix provided herein resemble that of rubber (elastomeric) under dry and/or wet conditions (e.g., soaked in an aqueous medium).

Unless explicitly stated otherwise, any reference to the elastomeric matrix provided herein is made to the elastomeric matrix under dry conditions. The term "dry conditions" refers to the elastomeric matrix provided herein itself, without referring to a solution that the matrix may or may not be soaked in/with. According to embodiments of the present invention, the elastomeric matrix provided herein is definable and shape-stable regardless of it being or not being soaked-in or wet with a liquid medium.

Water may be structurally fixed in the elastomeric matrix, may be free to evaporate/flow out of the matrix, or may not be present in the matrix. The exact amount of water (fixed and/or free) varies depending on the nature of the ingredients in the matrix and the conditions it is kept in. When referring to the "non-water" elements/ingredients of the elastomeric matrix provided herein, it is meant to refer to all its ingredients excluding water. The mass content of the "non-water" elements is not to be confused with the mass content of the matrix under dry conditions, which may include a mass of water.

When referring to "dry conditions" it should be taken as relating to conditions wherein the elastomeric matrix as provided herein is exposed to air at room temperature in an open or closed container and is not immersed in liquid, such as water or any other aqueous medium or liquid. In the context of ophthalmic devices, "dry conditions" describes a state that is the opposite of how contact lenses are stored; contact lenses are typically made of a hydrogel, which should always be kept under aqueous medium in order to retain their shape and malleability. In sharp contrast, the elastomeric matrix provided herein does not have to be kept wet and does not change its shape (although it may change in size) when going from wet to dry conditions and back.

Hence, when the elastomeric matrix is said to have less than 35% wt polyvinyl alcohol of the total weight of the non-water ingredients of the matrix, it is meant that the mass content of PVOH constitutes less than 35% wt of the total mass content of the matrix excluding any water, structurally fixed in the matrix (if any) or free to flow out of the matrix.

A relatively small amount of water in the matrix allows it to have longer shelf-life, and to be storable under dry conditions (i.e., not soaked in a liquid), whereas excessive amount of water is not required and undesired. Assuming only water evaporates from the wet elastomeric matrix, the amount of water remaining after conventional drying is seen as forming a part of the matrix. In the context of the present invention, conventional drying is drying by exposing the outer surface of the matrix to ambient air under room temperature and ambient humidity. The room temperature may range 15-30° C., and the relative humidity may range 30-75%. Exact conventional drying time may vary with the specific content of the matrix, but is typically between 24 hours and four days.

The amount of water can be determined, among other methods, by the Karl Fischer method, and the direct measurement of loss of mass upon drying, or LOD method. The Karl Fischer method was conducted volumetrically using Karl Fischer instrument model Titrando 852 (Metrohm), with Hydranal composite 5 (Honeywell) as titrant. Methanol was used as the solvent. The LOD test was conducted under a temperature of 85° C., using MX-50 moisture analyzer by A&D Company Ltd, Japan, on samples of 700 mg or larger.

According to these methods, which give similar results for a given sample, in some embodiments of the present invention, the elastomeric matrix includes less than about 50% wt of water therein. In some embodiments, the amount of water is less than about 40% wt, less than about 30% wt, less than about 25% wt, less than about 20% wt, less than about 15% wt, less than about 10% wt, or less than about 5% wt of the total mass of the matrix.

Due to its unique composition, the elastomeric matrix provided herein swells under wet conditions, while preserving its shape, by less than 50% in volume. In some embodiments, the matrix swells by no more than 40% by volume, or less than 35%, or less than 20%, or less than 15%, or less than 10%, or less than 5% by volume under wet conditions.

It is noted herein that the matrix may be cast, molded, cut or otherwise made with a distinct 3D shape, which essentially does not change when conditions change from dry to wet and vice versa. This property is referred to herein as shape retention. In other words, while the overall volume of a piece of the matrix provided herein may change (swell or shrink) under changing wetting conditions, the overall shape of the piece remains essentially the same, without distortions, compression or deformations. Hence, another characteristic of the elastomeric matrix provided herein is substantially uniform size variability along all directions and orientations under changing wetting conditions. Substantially uniform meaning that the size varies along each direction by the same amount±20%. This characteristic may also be referred to herein as isotropic swelling and shrinking.

The composition and method of preparing the elastomeric matrix provided herein also determine the degree of crystallinity of the matrix. Degree of crystallinity (DoC) is the fraction of the ordered molecules in a polymeric substance, which typically ranges between 10% and 80% for many known polymeric substances. Higher values can be achieved in materials having small molecules, or in polymeric substances prepared and/or stored at temperatures just under the melting point. Most methods of evaluating the degree of crystallinity assume a mixture of perfect crystalline and totally disordered areas; the transition areas are expected to amount to several percent. These methods include density measurement, differential scanning calorimetry (DSC), X-ray diffraction (XRD), infrared spectroscopy and nuclear magnetic resonance (NMR).

The elastomeric matrix provided herein does not require cooling to below room temperature and once set and dried, does not require heating to above room temperature. According to some embodiments, the degree of crystallinity of the matrix is lower than 70%, lower than 60%, lower than 50%, lower than 40%, lower than 30%, or lower than 20%.

The elastomeric matrix provided herein is highly suitable for use as an ophthalmic device in ophthalmic uses, including uses that require the matrix to be transparent and uses that do not pose such a requirement. Thus, the elastomeric matrix provided herein according to some embodiments, is characterized by relatively low transparency. The transparency of a substance refers to the optical distinctness with which an object can be seen when viewed through a film/sheet made from the substance. The transparency of an object made form the elastomeric matrix provided herein can be measured by its total transmittance, which is the ratio of transmitted light to the incident light, while accounting for influencing factors: reflection, absorption and dispersion. For example, subtracting the absorption/dispersion and reflection, the total transmittance of a sample is the incident light (100%) minus absorption/dispersion (X %) and minus reflection (Y %); in other terms, the total transmittance=incident light−(absorption/dispersion+reflection). In some embodiments, non-transparent elastomeric matrices may be preferred, e.g., due to being easier to produce without compromising functionality. For example, non-transparent elastomeric matrices may be obtained with PEG as a plasticizer and/or by producing the matrices at room temperature.

According to some embodiments of the present invention, the elastomeric matrix is characterized by total transmittance (transparency) through optical length of 0.5 a millimeter of less than 80%, less than 75%, less than 70%, less than 65%, less than 60%, less than 55%, less than 50%, less than 40%, or less than 30% total transmittance of light therethrough.

According to some embodiments of the present invention, PVOH used for preparing the elastomeric matrix provided herein is characterized by a degree of hydrolysis (D.H.) of more than 80%, more than 85%, more than 90%, or more than 95%. In some embodiments, the degree of hydrolysis of the PVOH is less than 100%.

The degree of polymerization (D.P.) of a polymer is estimated by dividing the molecular weight of the polymer by the molecular weight of the monomer unit. In some embodiments of the present invention, the PVOH that is used for preparing the elastomeric matrix provided herein is further characterized by a degree of polymerization of that ranges 500-5000. In some embodiments, the PVOH is a mix of different degrees of polymerization, for example, it may contain one PVOH with high molecular weight (e.g., chain length of 3000 monomers or more) and one PVOH of low molecular weight (e.g., of chain length of 1000 monomer or less).

In some embodiments, the elastomeric matrix provided herein is a non-biodegradable matrix. In some embodiments, the elastomeric matrix provided herein is a biodegradable matrix. In some embodiments, the elastomeric matrix is stable in liquid at room temperature more than 1 month. In some embodiments said elastomeric matrix undergoes, at least partially and gradually, dissolution and/or erosion when in contact with liquid (water, bodily fluids). In some embodiments, the elastomeric matrix provided herein is bio-erodible, namely the amount of polymer bulk in the matrix decreases, due to either physical, e.g., dissolution, and/or chemical processes occurring when the matrix is in contact with bodily tissues and/or bodily liquids. In some embodiments, said bodily liquid is tear fluid.

In some embodiments, the elastomeric matrix provided herein further comprises at least one inorganic ion and/or salts thereof, and/or at least one organic ion and/or salts thereof.

In some embodiments, the elastomeric matrix provided herein further comprises at least one buffering agent. In some embodiments, the buffering agent is tromethamine, potassium phosphate, citric acid, and any combinations thereof.

In some embodiments, the elastomeric matrix provided herein further comprises at least one surfactant. In some embodiments, the surfactant is selected from sorbitan esters (Spans), sorbitan tristearate (Tweens), poloxamers, Tritons, Betains and any combinations thereof.

In some embodiments, a matrix of the invention is substantially devoid of chemical (covalent) crosslinks.

Mechanical Properties:

The elastomeric matrix provided herein can substantially maintain its mechanical properties, such as rheological properties, elongation at break, tensile strength, yield strength, elongation at yield, elastic modulus and so forth, when exposed to wet conditions.

When referring herein to “dry conditions”, it should be understood to relate to conditions wherein a matrix of the invention is exposed to air at room temperature in an open or closed container and is not immersed in liquid, and particularly not in aqueous liquid. When referring to “wet conditions”, it should be understood to relate to conditions wherein a matrix of the invention is in direct contact with liquid (immersed in the liquid or after immersion in the liquid and before the liquid evaporated or wiped away).

In some embodiments, the liquid is a naturally occurring bodily fluid, including but not limited to blood, saliva, tears, excreta, body tissue, tissue fluids), an aqueous solution (e.g., of the at least one plasticizer), a buffer solution, and any combinations thereof. In some embodiments, the liquid is naturally occurring or simulating a naturally occurring fluid, such as artificial tear fluid. In some embodiments, a simulated tear fluid is based on an aqueous solution containing about 0.67% sodium chloride, about 0.2% sodium bicarbonate and about 0.008% calcium chloride.

In some embodiments, the elastomeric matrix provided herein is characterized by an elongation at break of at least 100%, 200%, 300%, 400%, 500%, 700%, at least 800%, or at least 900% under dry conditions. In some embodiments, the elongation at break of the matrix is at least 100% under wet conditions (immersed in liquid or after immersion in liquid).

It was surprisingly found that in some embodiments of the present invention wherein the water content was relatively low, the elongation at break was surprisingly high. Thus, according to some embodiments of the present invention, the elastomeric matrix having a water content of 30% wt or less, 25% wt or less, or 20% wt or less, exhibited relatively high elongation at break of 100% and higher, and even 300% and higher or 500% and higher.

In some embodiments, the elastomeric matrix provided herein is characterized by a tensile strength in the range 0.1 to 1.5 MPa or 0.05-2 MPa under dry conditions. [We have additional measurements that showed us 0.05 is a more proper lower limit.] In some embodiments, the elastomeric matrix provided herein is characterized by a tensile strength substantially in the range 0.1-0.4 MPa under wet conditions. In some embodiments, the tensile strength of the matrix is at least 0.1 MPa under wet conditions (immersed in liquid or after immersion in liquid).

In some embodiments, yield strength of the elastomeric matrix provided herein is at least 0.05-0.5 MPa under dry conditions. In some embodiments, yield strength of the elastomeric matrix provided herein is at least 0.01-0.5 MPa under wet conditions.

In some embodiments, the mechanical properties of the elastomeric matrix provided herein are maintained under dry conditions. In some embodiments, said mechanical properties are maintained under dry conditions for at least 1 year.

In some embodiments, the elastic modulus of the elastomeric matrix provided herein is at least 0.05-0.5 MPa under dry conditions. In some embodiments, the elastic modulus of the elastomeric matrix provided herein is at least 0.05-0.5 MPa under wet conditions. In some embodiments, the elastic modulus of the elastomeric matrix provided herein is at least 0.05 MPa, or at least 0.1 MPa or at least 0.2 MPa under dry conditions. In some embodiments, the elastic modulus of the elastomeric matrix provided herein is at least 0.05 MPa, or at least 0.1 MPa under wet conditions.

An exemplary elastomeric matrix, according to the fourth column in Table 1 below, was measured to have Young Modulus of 0.41 MPa, tensile strength of 0.51 MPa, and elongation at break of 456%.

Plasticizers:

The term “plasticizer”, as used herein, refers to a wide range of substances that together with PVOH bestow the mechanical properties of the elastomeric matrix provided herein. Without being bound by any particular theory, it is assumed that the PVOH and the plasticizer(s) interact and form a hydrogen-bonded network that allows the matrix to exhibit shape stability and elasticity under wet and dry conditions. The hydrogen bonded network may include plasticizer molecules linked to two (or more) PVOH residues.

In some embodiments of the present invention, the plasticizer is an organic materials, i.e., matter in its various forms that contain carbon atoms.

According to embodiments of the present invention, at least one of the plasticizers is characterized by exhibiting at least two hydrogen bond forming functional groups, namely at least two H-bond acceptors, at least two H-bond donors, or at least one H-bond acceptor and at least one H-bond donor.

According to some embodiments of the present invention, a plasticizer exhibits more than two H-bond forming functional groups, or more than 3, more than 4, more than 5, more than 6, more than 7, or more than 8 H-bond forming functional groups. In some embodiments, a plasticizer comprises a plurality of H-bond forming functional groups.

According to some embodiments, a plasticizer is characterized by a molar mass of less than 1,000 g/mol, or less than 500 g/mol. In some embodiments wherein the elastomeric matrix includes at least two plasticizers, the matrix may include at least one plasticizer which is an oligomer characterized by a molar mass of more than 1,000 g/mol. In some embodiments, the oligomer is characterized by a molar mass that ranges 1,000-2000 g/mol.

According to some embodiments of the present invention, a plasticizer is characterized by forming non-rigid cross-linked bridges with other elements of the matrix, such as PVOH. In this context, a plasticizer is characterized by exhibiting at least one, or at least two rotatable bonds in its structure, not including the bonds connecting the hydroxyl group to the molecule. In some embodiments, a plasticizer is characterized by exhibiting at least one bond having a variable dihedral angle. A dihedral angle is the angle between half-planes through two sets of three atoms, having two atoms in common. In some embodiments, the dihedral angle is defined between half-planes through two sets of three non-hydrogen atoms, having two non-hydrogen atoms in common. For example, ethylene glycol exhibits one variable dihedral angle which is defined by two sets of three atoms, each having an oxygen and two carbon atoms common to the two sets of non-hydrogen atoms.

In some embodiments, the plasticizers are biocompatible, namely the plasticizers do not elicit a non-tolerable local or systemic effect in a recipient/user. In some embodiments, a plasticizer is an ophthalmic compatible (acceptable) substance, namely it is biocompatible, and particularly does not elicit a non-tolerable ophthalmic effect in the recipient/user.

In the context of the present invention, according to some embodiments the elastomeric matrix comprises one or more plasticizer, and in other embodiments, the elastomeric matrix comprises at least two plasticizers. It is noted that when referring herein to a particular characteristic of a plasticizer, it is meant to be taken as referring to a single plasticizer or to each of the plurality of plasticizers individually.

According to some embodiments of the present invention, when the matrix includes more than one plasticizer, one is characterized by a viscosity that is at least 5-times higher than the viscosity of the other plasticizer. In some embodiments, at least one of the plasticizers is characterized by a viscosity of at least 1000 cp, and the other plasticizer is characterized by a viscosity of less than 200 cp. Alternatively, one plasticizer has a viscosity of 500 cp or above and the other 50 cp or below. For example, in one exemplary matrix, one of the plasticizers is glycerol, exhibiting a viscosity of about 1400 cp, and the other plasticizer is polyethylene glycol, exhibiting a viscosity of about 100 cp. In another example, one of the plasticizers is glycerol, and the other propylene glycol, exhibiting viscosity of about 40 cp.

In some embodiments, a plasticizer constitutes at least 30% wt, 40% wt, 50% wt, 60% wt, 70% wt, 80% wt, or at least 90% wt of the total weight of the matrix. In some embodiments, the plasticizer constitutes 30-90% wt of the weight of the matrix and any sub-range therebetween.

In some embodiments, the plasticizer is selected from polyols (e.g. ethylene glycol, diethylene glycol (DEG), triethylene glycol (TEG), and tetraethylene glycol), propylene glycols, glycerol, esters of glycerol (e.g. triacetin), polyprotic organic acids, e.g., oxalic acid, maleic acid, citric acid, etc.), polyamines (e.g., spermine, spermidine, diethylenetriamine, triethylenetetramine, tris(2-aminoethyl)amine, a polyethylenimine (PEI; polyaziridine, etc.), Trypan blue, alkyl gluceths, aliphatic polyether glycos (e.g., polyethylene glycol, prolypropylene glycol, polysorbate 80), polyoxyethylenes, ethanolamines, erythritols, tromethamine, urea, saccharides, amino acids (e.g., glycine, aspartate/aspartic acid etc.), polyphenols (e.g. tannic acid) and any combinations thereof.

In some embodiments, the plasticizer is an ophthalmic emollient or demulcent, as described by the FDA in 21 CFR 349.12. Thus, according to some embodiments of the present invention, the plasticizers are ophthalmic demulcents selected from the group consisting of cellulose derivatives, carboxymethylcellulose sodium, hydroxyethyl cellulose, hypromellose, hydroxypropyl cellulose, methylcellulose, hemicellulose, dextran, gelatin, liquid polyols, glycerin, polyethylene glycol 300, polyethylene glycol 400, polysorbate 80, propylene glycol, povidone, and any combination thereof.

In some embodiments, the matrix comprises glycerol as a single plasticizer. In some embodiments, the matrix comprises propylene glycol as a single plasticizer. In some embodiments, the matrix comprises glycerol and propylene glycol as plasticizers. In some embodiments, the matrix comprises glycerol and propylene glycol, each alone or a mixture thereof mixed with PEG, as plasticizers. In some of embodiments, PEG is used as a single plasticizer, and in some of these embodiments, the amount of PEG and the amount of PVOH are substantially the same.

Compositions of Elastomeric Matrices:

The invention further provides a composition of an elastomeric matrix immersed in liquid and/or combined with additional one or more elastomeric matrix(es), each of the matrixes being as disclosed herein.

In some embodiments, a composition of the invention comprises at least two elastomeric matrices as disclosed herein, which may be similar or different in composition, constitution and properties. In some embodiments, one formulation may be cast into a mold and let dry to provide an elastomer, and another solution may be cast above said elastomer to provide a bilayer elastomeric composition of matrices. In some embodiments, a plurality of minute elastomers of one kind (or of several kinds) may be mixed with a formulation that when settles provides an elastomer of another kind, so when the formulation settles it provides a "raisin cake" composition of the one or more elastomeric minute samples in a "dough" of another elastomer.

In some embodiments, the composition of the invention comprises a solution comprising at least one plasticizer, with at least one elastomeric matrix being immersed in said solution. In some embodiments, said composition of the invention further comprises a fluid selected from water or water-based solution or solvent, wherein said at least one elastomeric matrix is immersed in said fluid.

In some embodiments, said composition is stored, prior to use thereof, under dry conditions. In some other embodiments, said composition is stored, prior to use thereof, under wet conditions.

Composite Elastomeric Matrix:

While the elastomeric matrix provided herein can be prepared to suit the desired properties, some applications require the matrix to exhibit unique properties, which require to add another type of polymer(s) which is not PVOH, yet typically produced from hydrogen-forming monomers. This type of elastomeric matrices is referred to herein as a composite matrix.

In general, composite materials are the products of a connection between two different chemical entities. The connection between the different entities can be through covalent, non-covalent, ionic or other type or bond. The resulting properties sometimes represent a simple or complex weighted average of the individual properties of each ingredient, and sometimes products with very different properties from those of the two original components are obtained.

In the context of the present invention, it was found that by adding additional polymers that are not PVOH, new materials with a myriad of diverse characteristics can be obtained while keeping the basic characteristics of the elastomeric matric provided herein, namely low amount of polymers, softness, and shape retention under varying dry and wet conditions.

The addition of the non-PVOH polymer can be used for example in order to further modify:

stability in dry and wet conditions;
bio-degradability;
rheological properties;
bio-adhesiveness;
compatibility with active materials;
active material release profile; and
imprinting active materials.

In some embodiments, the composite elastomeric matrix is made by blending PVOH and a non-PVOH polymer capable of hydrogen bonding with PVOH. In some embodiments, said non-PVOH polymer is neutral (not charged). In some embodiments, said non-PVOH polymer has anionic or cationic functional groups (charged). In some embodiments, said non-PVOH polymer is a synthetic polymer. In some embodiments, said non-PVOH polymer is an oligosaccharide or polysaccharide. In some embodiments said non-PVOH polymer is an acrylic polymer.

It is clear to those skilled in the art that additional polymers and various types of molecular links (e.g. ionic, complexes etc.) can be used to create composite materials with PVOH, using either covalent or non-covalent interactions in order to connect the two polymers. The additional polymer that is not PVOH can be selected from various polymers, including naturally occurring polymers and macromolecules, synthetic polymers and the likes. For example, without limitation, the polymer of hydrogen bond forming monomers that is not PVOH is a polyacrylic acid, a polyvinyl pyrrolidone, cellulose, chitin, glycogen, starch, gellan, dextran, inulin, pectin, arabinoxylan, and any mixture thereof.

According to some embodiments of the present invention, the mass content of the non-PVOH polymer in the elastomeric matrix provided herein is smaller than the mass content of PVOH. In some embodiments, the mass ratio between PVOH and the non-PVOH polymer ranges from about 100:1 to 2:1. Some exemplary embodiments of composite matrices are provided in the Examples section that follows below.

Medical/Ophthalmic Device:

The present invention further includes the aspect of an ophthalmic/ocular device that can be used in treating ophthalmic/ocular pathologies and diseases, wherein the device comprises or consists of the elastomeric matrix provided herein.

In the context of the ophthalmic device, according to some embodiments of the present invention, the matrix comprises or consists of ophthalmically acceptable ingredients, as these are discussed hereinabove.

The elastomeric matrix provided herein is particularly useful for sequestering and eluding pharmaceutically active agents, since it is unreactive, stable and benign. The ophthalmic device that comprises the elastomeric matrix provided herein, is configured for drug delivery, both for bolus as well as for sustained release regimens. Hence, according to some embodiments, the matrix includes therein or thereon at least one pharmaceutically active agent. Preferably, the pharmaceutically active (therapeutic) agent is selected for treating an ophthalmic symptom, disease or disorder.

The ophthalmic device described herein is generally sized and shaped to be positioned on an outer surface of the eye with at least a portion of the ocular device positioned under one or both eyelids in a manner that does not contact or interfere with the cornea. In one aspect, the ophthalmic device provided herein is configured to be positioned on a surface of the eye, at least partially underneath at least one of the upper and/or lower eyelids and outside a cornea of the eye for delivering at least one therapeutic agent to an eye for an extended period of time.

The elastomeric matrix provided herein is characterized by a porous microstructure, which allows entrapping a liquid therein. The liquid may be, for example, a solution or a colloid comprising a pharmaceutically active agent, and this liquid can be dispersed in the matrix and/or entrapped in the pores of the matrix. Hence, in some embodiments, the device includes at least one therapeutic agent dispersed, sequestered, impregnated within the elastomeric matrix provided herein.

The pharmaceutically active agent can include, for example, a small molecule, a macromolecule, a cell or a tissue.

In some embodiments, the pharmaceutically active agent is in a liquid form. In some embodiments, the pharmaceutically active agent is in solid form. In some embodiments, the pharmaceutically active agent is soluble in water, or soluble in an organic solvent, or amphiphilic.

In some embodiments, the pharmaceutically active agent is encapsulated, or microencapsulated, or in a microparticle form, or in a nanoparticle form.

In the context of the present invention, the pharmaceutically active agent is, without limitation, an analgesic agent, an antacid, an antianxiety agent, an antiarrhythmic, an antibacterial agent, an antibiotic agent, an anticoagulant, a thrombolytic agent, an anticonvulsant, an antidepressant, an antiemetic agent, an antifungal agent, an antihistamine, an antihypertensive, an anti-inflammatory agent, an antineoplastic agent, an antipsychotic agent, an antipyretic agent, an antiviral agent, a barbiturate, a bronchodilator, a beta-blocker, a corticosteroid, a cold cure, a cytotoxic agent, a decongestant, a diuretic agent, a expectorant, a hormone, a hypoglycemic agent, an immunosuppressive agent, a laxative, a muscle relaxant, a sedative, a sex hormone, a sleeping drug, a tranquilizer, a vitamin, and any combinations thereof.

In some embodiments, the pharmaceutically active agent is an ophthalmological active agent. In some embodiments, the ophthalmological active agent is a lubricant, an anti-angiogenic agent, a mydriatic agent, an anesthetic, an anti-infective agent, an anti-inflammatory agent, an antihistamine, a glaucoma treatment agent, a surgical agent, a diagnostic agent or any combination thereof.

The pharmaceutically active agent can include, without limitation, bimatoprost, travoprost, latanoprost, tafluprost, NSAID, steroid, antihistamine, carbonic anhydrase inhibitor (CAI), dorzolamide, cyclosporine, antibiotic, doxycycline, tetracycline, azithromycin, fatty acid, long chain fatty acid, fatty alcohol, cetyl alcohol, stearyl alcohol, non-penetrating steroid, free acid of steroid, lipid, ketorolac, silicone oil, olopatadine, prostaglandin, prostaglandin analog, prostamide, small-molecule integrin antagonist, lifitegrast, loteprednol, and fluoromethalone or a combination thereof.

The pharmaceutically active agent can include a prostaglandin analogue. The prostaglandin analogue can include at least one of bimatoprost, latanoprost, travoprost, and tafluprost. The pharmaceutically active agent can be for lowering the intraocular pressure of the eye. The pharmaceutically active agent can be for treating dry eye. The pharmaceutically active agent can include at least one of cyclosporine, steroid, loteprednol, fluorometholone, non-penetrating steroid, free acid of steroid, nonsteroidal anti-inflammatory, ketorolac, small-molecule integrin antagonist, lifitegrast, doxycycline, azithromycin, lipid, fatty alcohol, cetyl alcohol, stearyl alcohol, fatty acid, long chain fatty acid, oil, or silicone oil. The pharmaceutically active agent can include a steroid. The steroid can include at least one of loteprednol or fluorometholone.

When preparing an ophthalmic device that comprises the elastomeric matrix according to some embodiments of the present invention, a formula is prepared according to the preparation procedure provided below. Briefly, a liquid formula is obtained which can be used to prepare the final device. The pharmaceutically active agent can be mixed into said liquid formula which leads to a matrix and a device that includes the pharmaceutically active agent. Hydrophilic pharmaceutically active agents easily dissolve in the formula, whereas hydrophobic pharmaceutically active agents may be suspended (e.g., as a colloid) in the formula.

The amount of the pharmaceutically active agent in the matrix depends on the pharmaceutically active agent and the treatment regimen. The nature of the matrix and the requirement therefrom, allow the matrix include 30% of its non-water constituents to be active agents.

In some embodiments, the matrix of the device further comprises at least one ophthalmically acceptable carrier/supplemental/adjuvant/additive/non-pharmaceutical agent.

The drug release profile depends on the pharmaceutically active agent, and the regimen. A skilled artisan would appreciate the means and technology present available for controlling sustained release of drugs from various devices and under various conditions. For example, encapsulation of pharmaceutically active agents, addition of materials that modifies the interaction between the agent and the matrix, and the likes.

In some embodiments, the pharmaceutically active agent is released from the matrix in the presence of a liquid, as this liquid is defined hereinabove. When referring to "presence of liquid" it should be understood to relate to the condition wherein the matrix of the invention is exposed to liquid, partially or entirely immersed therein.

In some embodiments, the pharmaceutically active agent is maintained within the elastomeric matrix under dry conditions. In some embodiments, the pharmaceutically active agent is maintained within the matrix during storage. In some embodiments, the pharmaceutically active agent is maintained within the matrix under dry conditions for at least 1 year.

Method of Treatment:

The elastomeric matrix of the present invention can be used for administration of pharmaceutically active agents to a cell or a tissue/membrane. The invention further provides a method of administering at least one pharmaceutically active agent to a cell or a tissue/membrane, which is realized by contacting the cell or tissue/membrane with a therapeutically effective amount of the pharmaceutically active agent present in the elastomeric matrix as disclosed herein. In some embodiments, the tissue is selected from ocular, orthodontic, muscle, mucosal, dermatological, connective, cardiac and any combinations thereof.

As used herein, the phrase "therapeutically effective amount" describes an amount of an active agent being administered, which will relieve to some extent one or more of the symptoms of the medical condition being treated. In the context of the present embodiments, the phrase "therapeutically effective amount" describes an amount of the pharmaceutically active agent being administered and/or re-administered, which will relieve to some extent one or more of the symptoms of the condition being treated by being at a level that is harmful to the target cell(s) or microorganism(s), and cause a disruption to the life-cycle of the target cell(s) or microorganism(s).

In the context of embodiments of the present invention, the therapeutically effective amount may refer to the pharmaceutically active agent as a whole or to the amount of one or more bioactive agent releasably sequestered in the matrix. The efficacy of any pharmaceutically active agent, can be determined by several methodologies known in the art.

According to another aspect of embodiments of the present invention, any one of the matrices described herein is identified for use in treating a subject diagnosed with a medical condition treatable by at least pharmaceutically active agent sequestered and controllably releasable from the matrix.

According to another aspect of embodiments of the present invention, there is provided a use of any of the elastomeric matrix described herein as delivery vehicle for use as a medicament. In some embodiments, the medicament is for treating a subject diagnosed with a medical condition treatable by at least one of the drugs sequestered and controllably releasable from the matrix.

In any of the methods and uses described herein, the matrix can be used for medicinal purposes as a part of a medical device.

Method of Preparation:

The present invention further provides a method of preparing the elastomeric matrix as disclosed herein, wherein the method comprises the steps of:

(a) dissolving polyvinyl alcohol in water to form a solution;
(b) optionally heating the solution;
(c) mixing the plasticizer(s) into the solution to form a mixture;
(d) optionally heating the mixture;
(e) adding the mixture into a mold;
(f) allowing the mixture set in the mold, to thereby form the elastomeric matrix of the invention.

In some embodiments, the solution obtained in (a) has less than 20% wt PVOH or less than 20% wt PVOH.

In some embodiments, the plasticizers make 30% wt or more of the mixture formed in (c).

In some embodiments of the method of preparing the matrix of the invention, the optional heating is achieved at a temperature ranging 60-100° C.

In further embodiments of the method, step (e) is conducted at room temperature, for example, after the mixture is let to cool while mixing. In some embodiments of the method, step (e) is conducted in an open form, e.g., in an open flask or mold. In some embodiments, the elastomeric matrix is poured into the mold. In some embodiments, the elastomeric matrix is pumped into the mold.

In some embodiments of the method, at least one pharmaceutically active agent is added to the solution, preferably, when the solution is at about room temperature, as not to encourage reactions between the active agent and other ingredients in the solution. This also allows using active agents that are heat sensitive.

In some embodiments of the method, the elastomeric matrix that is formed in step (f) is immersed, e.g., for 5 minutes, in a solution comprising at least one plasticizer or water or an aqueous solution or a solvent.

It is expected that during the life of a patent maturing from this application many relevant elastomeric matrices will be developed and the scope of the phrase "elastomeric matrix" is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non-limiting fashion.

Example 1

Preparation of an Elastomeric Matrix

The preparation of an elastomeric matrix according embodiments of the present invention, may start with the preparation of a PVOH solution.

Briefly, 420 ml of purified water were added into 500 ml round bottom flask equipped with an overhead stirrer. The flask was placed into a heating mantle, and 80 gr of PVOH were added in portions while stirring and heating until all the PVOH dissolved.

The PVOH solution was left to stir and heat for additional 1-2 hours, and thereafter the solution was left to cool to room temperature while stirring.

Plasticizers and 80 gr of the PVOH solution were added in a 500 ml glass beaker to obtain a mixture according to table 1 (dry matter basis). Optionally purified water was added to dilute concentration of solutes. The mixture was heated with magnetic stirring until fully dissolved, and thereafter heating was turned off and the mixture was left to cool.

Table 1 presents some exemplary formulations for preparing exemplary elastomeric matrices as provided herein. The values represent mass content in percent of the total weight of non-water ingredients.

TABLE 1

| | | | | | | | | | | | | | | |
|---|---|---|---|---|---|---|---|---|---|---|---|---|---|---|
| PVOH | 33 | 25 | 20 | 20 | 20 | 15 | 15 | 15 | 15 | 10 | 10 | 10 | 10 | 5 |
| Polyethylene glycol | 35 | 25 | 25 | 20 | 15 | | 10 | 5 | 20 | 15 | 10 | 20 | 5 | 5 |
| Glycerol | 20 | 25 | 30 | 60 | 34 | 35 | 30 | 40 | 30 | 37 | 40 | 35 | 37.5 | 45 |
| Propylene glycol | 12 | 25 | 25 | | 30 | 35 | 30 | 40 | 31 | 34 | 40 | 35 | 37.5 | 45 |
| Poly propylene glycol | | | | | | 15 | | | | | | | | |
| Kollicoat ® IR | | | | | | | 15 | | | | | | 10 | |
| Tromethamine | | | | | 1 | | | | | | | | | |
| Dextran | | | | | | | | | 4 | | | | | |

Example 2

Comparative Study

In order to study the criticality of the mass ratio between PVOH and the plasticizers, 20 gr of PVOH were mixed with 36 gr glycerol in a 500 ml glass beaker, and water was added thereto in order to achieve a solution of 20% wt PVOH. It is noted herein that this formulation for producing a matrix that is characterized by a mass content plasticizer to PVOH ratio of 36:20, namely 1:1.8, which is outside the scope of the present invention. The mixture was heated until complete dissolution. Heating was turned off and the solution was left to cool.

The resulting elastomeric matrix show inferior stability in both dry and wet conditions compared to a comparable matrix wherein the mass content ratio of plasticizer to PVOH is 2:1.

Another comparative example was prepared according to the procedure described hereinabove, using 35% wt of high molecular weight PVOH, 11% wt of polyethylene glycol, 27% wt of glycerol, and 27% wt of propylene glycol.

This formulation produced substances that exhibited swelling in water of more than 20%, and have not retained the shape it had under dry conditions.

Example 3

Preparation of Device

A solution of each of the various formulations specified in Table 1 was poured into a respective mold (open or closed) and left to dry. Optionally, a coating machine was used to create a film of desired thickness. The film was left to dry.

Example 4

Composite Elastomeric Matrices

To prepare a composite elastomeric matrix, according to some embodiments of the present invention, a formulation according to Table 1 was prepared and 10 gr of the formulation were mixed with a non-PVOH polymer in order to reach a ratio of polyvinyl alcohol to the non-PVOH polymer according to Table 2 below. The mixture was stirred until complete dissolution and further processed to create a device (e.g., a film).

TABLE 2

| Non-PVOH polymer | Ratio of PVOH to non-PVOH polymer |
|---|---|
| Sodium carboxymethyl cellulose (CMC Na) | 100:1 |
| Chitosan | 90:10 |
| Hydroxypropyl methylcellulose (HPMC) | 100:1 |
| Hydroxypropyl cellulose (HPC) | 100:1 |
| Polyvinyl pyrrolidone (PVP) | 75:25 |
| Polyacrylic acid | 75:25 |
| Dextran | 80:20 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

What is claimed is:

1. An ophthalmic device comprising an elastomeric matrix that comprises:

poly(vinyl alcohol) (PVOH), at least one plasticizer which is not water, and water, wherein:

a mass ratio of said plasticizer to said PVOH is at least 2:1; and a combined mass content of said PVOH and said plasticizer is at least 70-50% wt of the total weight of the matrix excluding said water.

2. The ophthalmic device of claim 1, wherein said at least one plasticizer comprises at least two plasticizers, none of which is water.

3. The ophthalmic device of claim 1, wherein the elastomeric matrix is characterized by substantially isotropic swelling and shrinking, wherein swelling and shrinking are such that dimensional changes measured along three mutually orthogonal principal dimensions of the matrix differ from one another by no more than ±20%, and wherein the dimensional changes are determined by comparing the dimensions of the matrix along each of the three mutually orthogonal principal dimensions in the matrix dry form prior to use to the dimensions of the matrix along each of the three mutually orthogonal principal dimensions while immersed in simulated tear fluid comprising an aqueous solution containing 0.67% sodium chloride, 0.2% sodium bicarbonate, and 0.008% calcium chloride.

4. The ophthalmic device of claim 1, wherein the elastomeric matrix is characterized by swelling by less than 50% by volume under wet conditions, wherein the volumetric swelling is determined by comparing a volume of the matrix in dry form prior to use to a volume of the matrix while immersed in a simulated tear fluid comprising an aqueous solution containing 0.67% sodium chloride, 0.2% sodium bicarbonate, and 0.008% calcium chloride.

5. The ophthalmic device of claim 3, wherein the elastomeric matrix is characterized by swelling by less than 50% by volume under wet conditions, wherein the volumetric swelling is determined by comparing a volume of the matrix in dry form prior to use to a volume of the matrix while immersed in the simulated tear fluid.

6. The ophthalmic device of claim 1, wherein said PVOH is characterized by a degree of hydrolysis of more than 90%.

7. The ophthalmic device of claim 2, wherein two of said at least two plasticizers are a polyol and a saccharide.

8. The ophthalmic device of claim 1, wherein said plasticizer or at least one of said plasticizers comprises at least two hydrogen bond forming functional groups.

9. The ophthalmic device of claim 1, wherein said plasticizer or at least one of said plasticizers is characterized by a molar mass of less than 1,000 g/mol.

10. The ophthalmic device of claim 1, wherein, when comprising more than one plasticizer, at least one of said plasticizers is an oligomer characterized by a molar mass of more than 1,000 g/mol.

11. The ophthalmic device of claim 1, wherein, when comprising more than one plasticizer, at least one of said plasticizers is characterized by a viscosity of at least 1000 cp, and at least one other of said plasticizers is characterized by a viscosity of less than 200 cp.

12. The ophthalmic device of claim 1, wherein said water constitutes less than 50% wt of the total mass content of said elastomeric matrix.

13. The ophthalmic device of claim 1, wherein said elastomeric matrix is essentially devoid of covalent crosslinking.

14. The ophthalmic device of claim 1, further comprising a pharmaceutically active agent.

15. The ophthalmic device of claim 1, configured to be positioned on a surface of an eye.

16. The ophthalmic device of claim 15, wherein said surface is at least partially underneath at least one of the upper and lower eyelids and outside a cornea of the eye.

17. The ophthalmic device of claim 1, configured to deliver at least one pharmaceutically active agent to an eye for an extended period of time.

18. The ophthalmic device of claim 1, wherein the combined mass content of the PVOH and the plasticizer is at least 70% wt of the total weight of the matrix excluding the water.

19. The ophthalmic device of claim 14, wherein the pharmaceutically active agent is selected from the group consisting of a prostaglandin analog, a prostamide, a carbonic anhydrase inhibitor, a beta-adrenergic antagonist, a corticosteroid, a non-steroidal anti-inflammatory drug, an antihistamine, an antibiotic, an anti-infective agent, and a small-molecule integrin antagonist, and combinations thereof.

20. The ophthalmic device of claim 14, wherein the pharmaceutically active agent is selected from the group consisting of bimatoprost, travoprost, latanoprost, tafluprost, dorzolamide, cyclosporine, lifitegrast, loteprednol, fluoromethalone, ketorolac, olopatadine, doxycycline, tetracycline, azithromycin and combinations thereof.

* * * * *